United States Patent
Scheuring et al.

(10) Patent No.: US 9,220,693 B2
(45) Date of Patent: Dec. 29, 2015

(54) AQUEOUS COMPOSITION COMPRISING BROMHEXINE

(75) Inventors: Uwe Scheuring, Ingelheim am Rhein (DE); Bernd Plohmann, Ingelheim am Rhein (DE); Annette Zamponi, Ingelheim am Rhein (DE)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 247 days.

(21) Appl. No.: 13/808,417

(22) PCT Filed: Jul. 7, 2011

(86) PCT No.: PCT/EP2011/061527
§ 371 (c)(1),
(2), (4) Date: Mar. 20, 2013

(87) PCT Pub. No.: WO2012/007352
PCT Pub. Date: Jan. 19, 2012

(65) Prior Publication Data
US 2013/0267605 A1 Oct. 10, 2013

(30) Foreign Application Priority Data
Jul. 12, 2010 (EP) .................................. 10169236

(51) Int. Cl.
*A61K 31/137* (2006.01)
*A61K 9/00* (2006.01)
*A61K 9/08* (2006.01)

(52) U.S. Cl.
CPC ............. *A61K 31/137* (2013.01); *A61K 9/0095* (2013.01); *A61K 9/08* (2013.01)

(58) Field of Classification Search
CPC ...... A61K 31/137; A61K 9/0095; A61K 9/08
See application file for complete search history.

(56) References Cited

U.S. PATENT DOCUMENTS

| 5,624,906 A * | 4/1997 | Vermeer .................... 514/23 |
| 2003/0157033 A1 * | 8/2003 | Endo .................... 424/49 |
| 2013/0267605 A1 | 10/2013 | Scheuring et al. |

FOREIGN PATENT DOCUMENTS

| EP | 0896815 A1 | 2/1999 |
| EP | 1121940 A1 | 8/2001 |
| WO | 03030877 A1 | 4/2003 |
| WO | 2012007352 A1 | 1/2012 |

OTHER PUBLICATIONS

Machine Translation of JP 2001-106639. Translated Nov. 1, 2014. Original Publication Date: Apr. 17, 2001.*
Database WPI; Week 200145; Thomson Scientific, London, GB; AN 2001-420810; JP 2001 106639, Taisho Pharm. Co. Ltd.; Apr. 17, 2001; abstract.
Database WPI; Week 200981; Thomson Scientific, London, GB; AN 2009-R19749; KR 2009 115 359, ELT Sci. Corp; Nov. 5, 2009; abstract.
Database EPODOC; European Patent Office; The Hague, NL; Aug. 22, 2007; "Composition and great volume injection containing bromhexine salt and the injection preparing process"; Database accession No. CN101019826; abstract; CN 101 019 826; Zhang Song; Aug. 22, 2007; entire document.
International Search Report, Form PCT/ISA/210, for corresponding PCT/EP2011/061527; date of mailing: Dec. 16, 2011.

* cited by examiner

*Primary Examiner* — Sreeni Padmanabhan
*Assistant Examiner* — Jody Karol
(74) *Attorney, Agent, or Firm* — Michael P. Morris; Mary-Ellen M. Devlin

(57) ABSTRACT

The present invention relates to aqueous compositions containing bromhexine, the composition comprising an amount of sugar alcohols of less than 10 g based on 100 ml of the composition, and the use thereof for secretolytic therapy in acute and chronic bronchopulmonary disorders.

7 Claims, No Drawings

AQUEOUS COMPOSITION COMPRISING BROMHEXINE

It is known that bromhexine is a synthetic derivative of the plant-derived active substance vasicine. It has a secretolytic and secretomotor effect in the region of the bronchial tract. Clinical trials have shown that it alleviates coughing and assists expectoration. By reducing viscosity and activating the ciliated epithelium it promotes the elimination of mucus. Consequently, bromhexine is used for secretolytic therapy in acute and chronic bronchopulmonary diseases associated with disorders of mucosal formation and transport.

It is also known that bromhexine hydrochloride is subject to a slow decomposition process during storage. According to the European Monograph on Bromhexine Hydrochloride (Ph Eur monograph 0706), the decomposition products are, in particular, (A) (2-amino-3,5-dibromophenyl)methanol, (B) 2-amino-3,5-dibromo-benzaldehyde, (C) N-(2-aminobenzyl)-N-methylcyclohexanamine, (D) N-(2-amino-5-bromobenzyl)-N-methylcyclohexanamine and (E) (3RS)-6,8-dibromo-3-cyclohexyl-3-methyl-1,2,3,4-tetrahydroquinazolin-3-ium.

For stabilising a composition containing bromhexine, JP 10101581 teaches the use of reducing agents and/or chelating complexing agents.

JP 200281562 and JP 2007119453 teach the use of sugar alcohols for stabilising a composition containing bromhexine. JP 63313725 teaches maltitol as a particularly suitable stabiliser. JP 10036292 and JP10306038 teach, as a further advantage of the sugar alcohols, the fact that they mask the bitter intrinsic flavour of bromhexine.

A particularly stable aqueous composition containing bromhexine is marketed under the name Bisolvon® Cough Syrup (solution to be taken). This composition contains bromhexine hydrochloride (8 mg/5 ml), maltitol syrup, benzoic acid, levomenthol, sucralose, flavourings and purified water.

The problem of the present invention was to provide an aqueous solution of bromhexine that is characterised by a particularly high stability, i.e. by a particularly low decomposition rate of bromhexine. This is intended in particular to produce a composition that is suitable for packing in foil packages. In addition, the composition according to the invention should if possible be characterised in that it adequately masks the bitter taste of bromhexine. Furthermore, the composition according to the invention should if possible also be characterised by a texture that gives a suitable mouth feel.

According to the invention these problems are solved by an aqueous composition containing bromhexine, the composition containing a quantity of sugar alcohols of less than 10 g, based on 100 ml of composition, dissolved therein.

The compositions according to the invention are surprisingly characterised, in spite of the small amount of sugar alcohols suitable for stabilisation, by a very low decomposition rate for the bromhexine. Consequently, there is no need for the addition of reducing agents and/or chelate complexing agents taught in the prior art.

The compositions according to the invention are particularly suitable as a cough elixir or cough syrup, because of the known effect of bromhexine.

Accordingly, in another aspect, the present invention relates to the use of a composition according to the invention as defined herein for secretolytic therapy in acute and chronic bronchopulmonary diseases.

Within the scope of the present invention the term "bromhexine" denotes N-(2-amino-3,5-dibromobenzyl)-N-methylcyclohexanamine hydrochloride.

Usually, the compositions according to the invention contain bromhexine in an amount of 0.04 to 0.4 g based on 100 ml of the composition. The amount of bromhexine specified in each case refers to the quantity of the salt used. Preferably, the compositions according to the invention contain bromhexine in an amount of 0.08 bis 0.32 g, for example in an amount of 0.16 g, based in each case on 100 ml of the composition.

A particular embodiment of the present invention relates to compositions according to the invention which contain bromhexine as the sole active ingredient, i.e. so-called monopreparations.

Within the scope of the present invention the term "sugar alcohol" denotes compounds that may be obtained by reduction of a saccharide, particularly a mono- or disaccharide. Examples of sugar alcohols conventionally used as additives in pharmaceutical compositions include sorbitol, xylitol, maltitol, isomalt, mannitol, threitol, erythritol and arabitol.

The quantity of sugar alcohols in the compositions according to the invention is less than 10 g based on 100 ml of the composition. Preferably, the amount of sugar alcohols in the compositions according to the invention is less than 5 g and most preferably less than 1 g, in each case based on 100 ml of the composition. One particular embodiment of the invention relates to compositions that are free from sugar alcohols.

Within the scope of the present invention the term "aqueous compositions" denotes liquid compositions the solvent of which consists of at least 50% by weight of water. The remainder of the solvent is conventionally selected from among the alcohols such as ethanol, polyethyleneglycol (macrogol), propyleneglycol and glycerol. However, the term "aqueous compositions" preferably denotes compositions in which the solvents consist of at least 80% by weight and more preferably at least 90% by weight of water. One particular embodiment relates to a composition according to the invention wherein the solvent consists exclusively of water. Such compositions are alcohol-free and are thus fundamentally suitable for use in children.

The proportion of solvent in the composition according to the invention is usually at least 50% by weight. The compositions according to the invention are preferably characterised by a solvent content of at least 70% by weight and most preferably at least 80% by weight. The compositions according to the invention also allow a solvent content of at least 90 or at least 95% by weight, owing to the fact that they do not contain sugar alcohols for stabilisation.

Usually, the compositions according to the invention contain a suitable thickener. In this way the compositions according to the invention can be adjusted to the required viscosity depending on the desired form of preparation. As a result, the compositions according to the invention contain the thickener in an amount that is suitable for achieving the desired viscosity. Usually, the compositions according to the invention contain the thickener in an amount of 0.05 to 5 g, based on 100 ml of the composition according to the invention. Suitable thickeners are selected for example from among hydroxypropylmethylcellulose (HPMC), hydroxyethylcellulose (HEC), hydroxypropylcellulose (HPC), methylcellulose (MC), carboxymethylcellulose (CMC), and methylethylcellulose (MEC). Preferably the thickeners are selected from among hydroxypropylmethylcellulose (HPMC), hydroxyethylcellulose (HEC) and hydroxypropylcellulose (HPC). In particular the thickener used according to the invention is hydroxyethylcellulose.

The compositions according to the invention are usually characterised by a viscosity in the range from 50 mPas to 30 Pas at a temperature of 20° C.

One particular embodiment relates to a composition according to the invention wherein the composition is a cough elixir or cough syrup. These special preparation forms usually have a viscosity of at least 100 mPas and in particular at least 120 mPas, at a temperature of 20° C. in each case. The amount of thickener present is usually in the range from 0.1 to 1 g based on 100 ml of the composition according to the invention.

Usually the compositions according to the invention contain a suitable sweetener. Preferably, according to the invention, sweeteners are used which are different from sugar alcohols, i.e. in this embodiment the compositions according to the invention are free from sugar alcohols.

Suitable sweeteners are selected for example from among sucralose, acesulfame, aspartame, cyclamate, saccharin, isomalt, maltitol, xylitol, lactitol, erythritol, alitame, thaumatin and neohesperidin dihydrochalcone. Preferably, sucralose, acesulfame, aspartame, cyclamate, saccharin, alitame, thaumatin and neohesperidin dihydrochalcone are used. The sweetener sucralose is particularly preferred.

The compositions according to the invention usually contain the sweetener in an amount of 0.01 g to 10 g based on 100 ml of the composition. Preferably, the compositions according to the invention contain the sweetener in an amount of 0.1 to 1 g and particularly preferably in an amount of 0.1 to 0.5 g, in each case based on 100 ml of the composition according to the invention.

Usually, the compositions according to the invention contain a suitable preservative.

For reasons of clarity the term "preservative" as used herein does not refer to sugar alcohols, which are also known to have a preservative effect.

Examples of suitable preservatives include benzoic acid, sorbic acid, sulphuric acid or the salts thereof. Benzoic acid, in particular, has proved a suitable preservative for compositions containing bromhexine.

The compositions according to the invention usually contain the preservative in an amount of 0.005 to 0.5 g based on 100 ml of the composition. Preferably, the compositions according to the invention contain the preservative in an amount of 0.01 to 0.1 g, particularly preferably 0.02 to 0.05 g, based on 100 ml of the composition in each case.

Usually the compositions according to the invention have a pH in the range from 2.0 to 6.0, preferably from 2.5 to 4.5. Particularly preferably, the pH of the compositions according to the invention is in a range from 3.0 to 4.0.

Suitable acid regulators are for example malic acid, fumaric acid, lactic acid, citric acid, tartaric acid, orthophosphoric acid, metatartaric acid, adipic acid or succinic acid.

If an acid or its salt is used as a preservative in the compositions according to the invention, there is normally no need to use an additional acid regulator. In this particular embodiment the composition according to the invention therefore does not usually contain an acid regulator.

In another preferred embodiment the composition according to the invention does not contain any reducing agents and/or chelating complexing agents such as tartaric acid, EDTA or the like.

Composition according to one of the preceding claims, consisting of:
 a) bromhexine in an amount of 0.04 g to 0.4 g,
 b) thickener in an amount of 0.005 g to 5 g,
 c) sweetener in an amount of 0.01 g to 10 g,
 d) other suitable additives selected from among preservatives, acid regulators, antifoamers, flavourings and colourings, in an amount of 0 to 10 g and
 e) water ad 100 ml.

With regard to the preferred quantity and nature of the components of this special embodiment, the remarks made earlier apply.

Suitable antifoamers such as simethicone, for example, are known to the skilled man.

Suitable flavourings and colourings are known to the skilled man.

The compositions according to the invention are prepared by conventional formulation techniques. It is not critical whether the components of the composition according to the invention are mixed together simultaneously or successively. Equally, the order in which it is done is not important. The ingredients of the composition according to the invention may be prepared in pure form, in the form of solutions, or in the form of partial compositions which already contain several ingredients of the composition according to the invention.

Thanks to their high stability the compositions according to the invention are suitable for transferring into all conventional packaging forms. In particular, by virtue of their high stability, the compositions according to the invention are also suitable for transferring into chemically inert foil packs, besides conventional bottling in glass containers. Suitable foils are commercially obtainable. In particular, laminated foils such as those that are commercially obtainable under the brand names Aclar® or Barex® for example are suitable for foil packaging of the compositions according to the invention.

The invention is hereinafter explained in more detail by means of non-restrictive Examples.

EXAMPLES

(A) Preparation Example

Hydroxyethylcellulose was added to 60 ml of water with stirring at 20-25° C. The mixture thus obtained was stirred for a further 30 min. and then heated to about 85° C. with stirring over a period of 60 min. Then benzoic acid (25.4 mg) was added and the mixture was stirred for a further 10 min. Next, 35 ml of water were added and the solution was cooled to 60° C. Bromhexine hydrochloride (160 mg) was added and the mixture was stirred for 20 min. Then the solution was cooled to 50° C., sucralose (225 mg) was added and the mixture was stirred for 10 min. After this the mixture was cooled to ambient temperature and flavourings (41 mg) were added. After another 30 min. with stirring the mixture was topped up to a total volume of 100 ml by the addition of water. Then the composition obtained was stirred for 10 min., filtered and packed into sachets on the packing machine or bottled in brown glass bottles.

The composition according to the invention thus obtained has a viscosity of 135 mPas. The viscosity was determined at a temperature of 20° C. using a falling ball viscometer according to the method described in the European Pharmacopoeia (European Pharmacopoeia, 6th edition, page 84, chapter 2.2.49).

(B) Investigations of Stability

To investigate the stability the composition obtained in (A) and a composition corresponding to Bisolvon® Cough Syrup (Comparison Example) were each packaged in a foil pack (made from Barex® foils produced by DanaPak) and in a standard commercial brown glass bottle. The stability of the composition under controlled storage conditions (30° C., 75% r.h.) was evaluated using the decomposition product E ((3RS)-6,8-dibromo-3-cyclohexyl-3-methyl-1,2,3,4-tetrahydroquinazolin-3-ium) described in the European Monograph. To do this the content of decomposition product E in the samples was determined by HPLC and UV detection.

The results of this investigation are compiled below.

a) Bisolvon® Cough Syrup (Comparison Example)

Composition: bromhexine hydrochloride (0.16 g/100 ml), maltitol liquid (50 g), benzoic acid (0.13 g/100 ml), flavourings, water.

| Foil packaging: | 12 days | 1 month, 30° C./75% r.h. |
|---|---|---|
| Decomposition product E: | 0.16% | 0.21% |
| Other decomposition products: | not detectable | <0.05% |
| Brown glass bottle: | 12 days | 1 month, 30° C./75% r.h. |
| Decomposition product E: | 0.16% | 0.21% |
| Other decomposition products: | not detectable | <0.05% | b) Composition According to the Invention

Composition: according to the Preparation Example (A).

| Foil packaging: | 0 days | 1 month 30° C./75% r.h. |
|---|---|---|
| Decomposition product E: | <0.05% | 0.07% |
| Other decomposition products: | not detectable | 0.07% |
| Brown glass bottle: | 0 days | 1 month 30° C./75% r.h. |
| Decomposition product E: | <0.05% | <0.05% |
| Other decomposition products: | 0.08% | not detectable |

The test results show that the compositions according to the invention are distinguished from the standard commercial compositions containing bromhexine by a particularly low decomposition rate for the bromhexine.

The invention claimed is:
1. An aqueous composition consisting of:
 a. bromhexine in an amount of 0.04 g to 0.4 g,
 b. thickener in an amount of 0.005 g to 5 g,
 c. sweetener in an amount of 0.01 g to 10 g,
 d. other suitable additives selected from among preservatives, acid regulators, antifoamers, flavorings and colorings in an amount of 0 to 10 g, and
 e. water ad 100 ml
 wherein the composition contains an amount of sugar alcohol of less than 10 g based on 100 ml of the composition.
2. The composition according to claim 1, wherein the composition has a viscosity in the range from 50 mPas to 30 Pas at a temperature of 20° C.
3. The composition according to claim 1, containing a suitable preservative.
4. The composition according to claim 3, wherein the preservative is present in an amount of 0.01 g to 0.5 g based on 100 ml of the composition.
5. The composition according to claim 1, wherein the composition has a pH in the range from 2.0 to 6.0.
6. The composition according to claim 1, wherein the composition has a water content of at least 70% by weight.
7. The composition according to claim 1, wherein the composition is a cough elixir or cough syrup.

* * * * *